United States Patent [19]

Shetty et al.

[11] 4,395,552
[45] Jul. 26, 1983

[54] ANTIMICROBIAL BIS-IMIDAZOLO-PYRIDINE COMPOUND

[75] Inventors: Bola V. Shetty, Stamford, Conn.; John E. Airey, Mt. Kisco, N.Y.

[73] Assignee: The Purdue Frederick Company, Norwalk, Conn.

[21] Appl. No.: 203,480

[22] Filed: Nov. 3, 1980

Related U.S. Application Data

[62] Division of Ser. No. 92,279, Nov. 8, 1979, Pat. No. 4,281,138.

[51] Int. Cl.³ .......................................... C07D 471/04
[52] U.S. Cl. .................................................. 546/118
[58] Field of Search ........................................ 546/118

[56] References Cited

U.S. PATENT DOCUMENTS 3,590,045  6/1971  Vogt .................................... 546/118

FOREIGN PATENT DOCUMENTS 41-16517  9/1966  Japan .

Primary Examiner—Jane T. Fan
Attorney, Agent, or Firm—Steinberg & Raskin

[57] ABSTRACT

Antimicrobial compounds of the formulae:

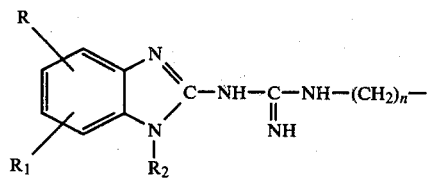

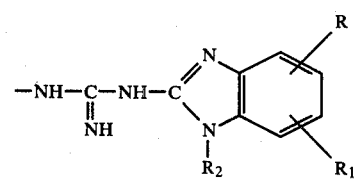

and

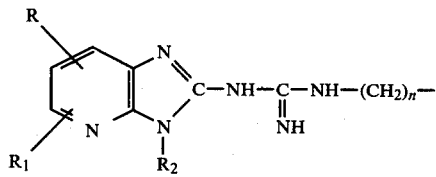

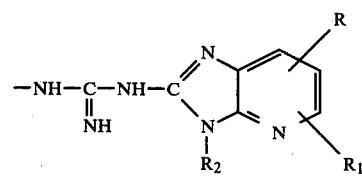

wherein R and $R_1$ = H, lower alkyl, halogen, methoxy, hydroxy, nitro, carboxy, aryl (preferably phenyl) substituted aryl (preferably substituted by lower alkyl) and sulfamyl, $R_2$ = hydrogen, lower alkyl, aryl (preferably phenyl) and substituted aryl (preferably substituted by lower alkyl) and wherein n is an integer from 2–20, are provided. Also provided are the method of producing such compounds.

2 Claims, No Drawings

ANTIMICROBIAL BIS-IMIDAZOLO-PYRIDINE COMPOUND

This is a division of application Ser. No. 92,279, filed 11/8/79 now U.S. Pat. No. 4,281,138.

BACKGROUND OF THE INVENTION

Antimicrobial compounds include a broad range of diverse chemical compounds which are capable of destroying microbes either through a cidal or killing action or by a stassis effect which inhibits further growth of the organisms to enable other defense mechanisms to destroy the same.

Irrespective of the particular mode of action, antimicrobial compounds have a desirable use in virtually every field of commerce from agronomy to zoology. Literally thousands of chemical compounds are known to have germicidal properties and hundreds of chemical agents are now utilized commercially for this purpose.

Unfortunately, many of these compounds are not effective in the presence of organic materials and others cause excessive damage to tissues and other living things. Although tissue damage is of little concern when antiseptic agents are utilized for disinfection of inanimate objects, other limitations such as corrosion, staining and other noxious effects become important considerations. On the other hand, tissue damage per se is a serious concern when a germicidal agent is used to combat disease of plants, animals and humans.

It is commonly believed that effective antiseptics are non-selective and that they have a universal spectrum of activity against all germs. Although this is generally true, it is important to note that significant exceptions do exist and that the relative susceptibility of microorganisms to a particular chemical compound are especially desirable. For example, hexachlorophene is primarily effective against gram-positive organisms and not effective against gram-negative organisms. Cationic antiseptic agents are not active against sporolating organisms. Certain bacteria are even capable of growing in 70% alcohol, whereas other germicides are inert to fungi and spores and antifungal agents are not bactericides.

Thus, the selectivity of an antiseptic germicidal compound is important and desirable. Those agents which are selective are unique since this type of target germicidal activity permits the destruction of an invading microbe without affecting the benign desirable microbial flora commonly found in the healthful environment. Unfortunately, however, there is not means by which the germicidal activity of a chemical compound may be predetermined or predicted to obtain a selective effect.

SUMMARY OF THE INVENTION

It is accordingly a primary object of the present invention to provide a series of compounds which have a selective antimicrobial antiseptic and disinfectant action without having noxious properties.

It is another object of the present invention to provide compounds with selective microbicidal activity without the broad spectrum germicidal action that is expected for topical antibacterial agents.

It is yet a further object of the present invention to provide a series of compounds having these properties and to provide for the production of such compounds.

With the above and other objects in view, the present invention will be apparent from a further reading of the specification and of the appended claims.

With the above and other objects in view, the present invention comprises compounds of the general formulae:

Antimicrobial compounds of the formulae:

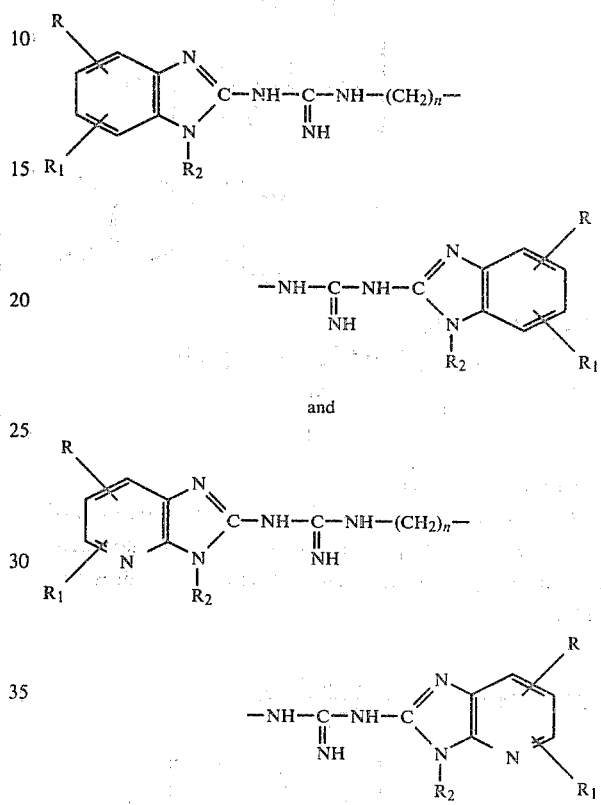

wherein R and $R_1$ = H, lower alkyl, halogen, methoxy, hydroxy, nitro, carboxy, aryl (preferably phenyl) substituted aryl (preferably substituted by lower alkyl) and sulfamyl, and $R_2$ = hydrogen, lower alkyl, aryl (preferably phenyl) and substituted aryl (preferably substituted by lower alkyl) and wherein n is an integer from 2–20, are provided. Also provided are the method of producing such compounds.

The above compounds, have selective antimicrobial antiseptic and disinfectant action without noxious properties.

The in vitro spectrum of activity shown by these compounds indicates that the same have a selective microbicidal activity without the broad spectrum germicidal action normally expected for topical antibacterial agents. Thus, for example, certain compounds of the invention are active against diplococcus pneumoniae but not against Klebsiella pneumonia. On the other hand, other compounds are found to possess selective activity against streptococcus pyogenes and salmonella typhosa without possessing broad germicidal properties.

Upon oral administration of the above compounds to mice, the $LD_{50}$ is determined to be greater than 4 gm/kg which indicates negligible toxicity and a high degree of safety since the minimum inhibitory concentration (mic) for these compounds is less than 32 parts per million.

The compounds of the present invention may generally be prepared in accordance with the following general scheme:

General Synthetic Scheme

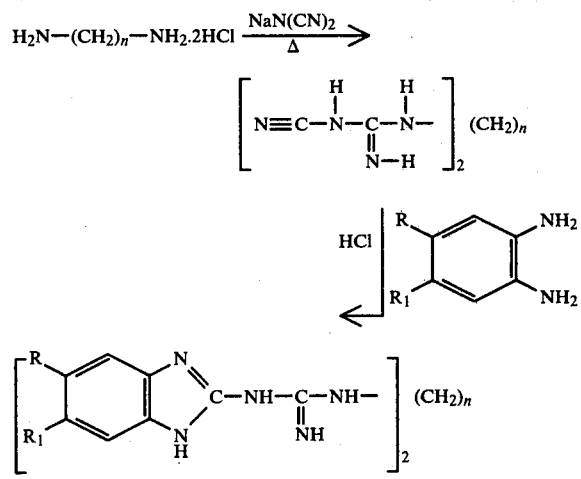

wherein X=C or N.

The following equations illustrate the production of the specific compound N'-N''-bis-[2-(6-chlorobenzimidazalyl)]-2,9-diazadecane diimidamide dihydrochloride:

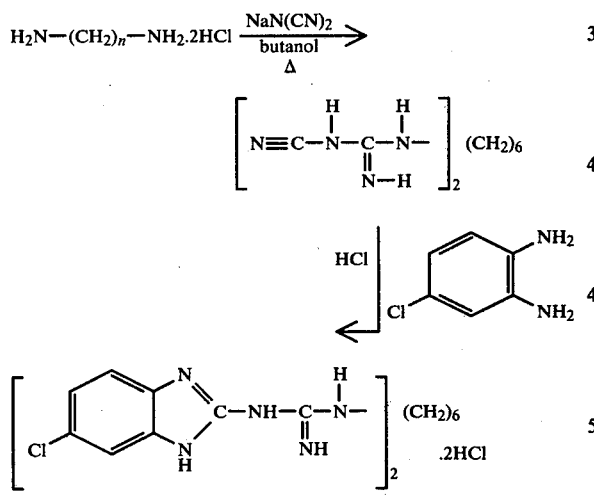

Other compounds are produced in similar manner.

The compounds listed in Table I below were tested for their antibacterial spectrum by the method of:

Silverblatt, F. and M. Turck, 1969. Antimicrobial Agents and Chemothreapy; 1968, p. 279-285.

Wallace, J. F., E. Atlas, D. M. Bear, N. K. Brown, H. Clark and M. Turk, 1971. Antimicrobial Agents and Chemotherapy; 1970, p. 223-266. The results of this testing are described in Table I. The antimicrobial profile exhibited in terms of minimum inhibitory concentration indicates a highly selective action for these compounds.

TABLE I

MINIMUM INHIBITORY CONCENTRATION (MIC*) (32 P.P.M.)

| Compound | − Escherichia coli | − Pseudomonas aeruginosa | + Staphylococcus aureus | F Candida albicans | − Proteus mirabilis | − Serratia marcescens | Funghi Aspergillus niger |
|---|---|---|---|---|---|---|---|
| 1081 | 1 | 8 | 1 | 8 | N.A. | N.A. | N.A. |
| 1080 | 1 | N.A. | 1 | N.A. | N.A. | N.A. | N.A. |
| 1075 | 2 | N.A. | 2 | N.A. | N.A. | N.A. | N.A. |
| 1074 | 4 | 8 | 8 | 16 | N.A. | N.A. | N.A. |
| 1024 | 4 | 16 | 4 | N.A. | N.A. | N.A. | N.A. |
| 1072 | 4 | 16 | 16 | N.A. | N.A. | N.A. | N.A. |
| 1046 | 8 | N.A. | 8 | 16 | N.A. | N.A. | N.A. |
| 1079 | 8 | N.A. | 8 | N.A. | N.A. | N.A. | N.A. |
| 1045 | 8 | N.A. | N.A. | N.A. | N.A. | N.A. | N.A. |
| 1069 | 32 | N.A. | N.A. | N.A. | N.A. | N.A. | N.A. |
| 1105 | N.A. | N.A. | 5 | N.A. | N.A. | N.A. | N.A. |

*MIC - Parts Per Million
1024 + Diplococcus pneumoniae = 2 ppm
+ Streptococcus pyogenes = 1
− Salmonella typhosa = 4
− Klebsiella pneumonia = 500
$LD_{50}$ = 4 Gm/Kg orally The specific compounds referred to by compound number are identified in the examples which follow.

DESCRIPTION OF PREFERRED EMBODIMENTS

The following examples are given to further illustrate the present invention. The scope of the invention is not, however, meant to be limited to the specific details of the examples:

EXAMPLE 1

N'-N''-bis[2-(6-chlorobenzimidazole)]-2,9-diazadecane diimidamide dihydrochloride 4-chloro-o-phenylenediamine [21.3 gm., 0.15 mole] and 1,6-di($N^3$-cyano-N'-guanidino) hexane [18.75 gm., 0.075 mole] were finely ground in a mortar and pestle. The intimate mix was refluxed with water [150 ml] and concentrated hydrochloric acid [30 ml] for 6 hours. The solution was allowed to cool to room temperature over 70 hours. The greyish solid was filtered from the dark solution, washed with a little water and air dried. The solid was then washed with ethanol till no more color was removed. The grey solid was air dried, then dried under vacuum at 100° C. for 24 hours. The grey solid [10.0 gm] had melting point of 241°-243° C.

| Analysis: | C | H | Cl | N |
|---|---|---|---|---|
| Calculated for $C_{22}H_{26}N_{10}Cl_2$ 2HCl | 45.99 | 4.88 | 24.74 | 24.32 |
| Found: | 45.98 | 4.84 | 24.40 | 24.32 |

EXAMPLE 2

N'-N''-bis[2-(6-nitrobenzimidazole)]-2,9-diazadecane diimidamide 4-nitro-o-phenylenediamine [30.6 gm., 0.2 mole] and 1,6-di($N^3$-cyano-N'-guanidino) hexane [25.0 gm., 0.1 mole] were finely ground in a mortar and pestle. The intimate mix was refluxed with water [200 ml] and concentrated hydrochloric acid [40 ml] for 4 hours. The reaction mixture was allowed to cool to room temperature and the yellowish solid filtered, washed well with water, then ethanol until no more color was removed. The solid was air dried, then dried under vacuum at room temperature, to give a yellow solid [25 gm] as the dihydrochloride. The hydrochloride salt [5.0 gm] was stirred at room temperature with 10% aqueous sodium hydroxide. The orange solid was well washed with water, air dried, then dried over refluxing xylene and under vacuum for 5 hours. The orange solid [4.4 gm] had melting point 254°–260° C. with decomposition.

| Analysis: | C | H | N |
|---|---|---|---|
| Calculated for $C_{22}H_{26}N_{12}O_4 \cdot 1\frac{1}{2} H_2O$ | 48.09 | 5.28 | 30.60 |
| Found: | 48.15 | 4.91 | 30.42 |

EXAMPLE 3

N'-N''-bis-[2-benzimidazole]-2,9-diazadecane diimidamide dihydrochloride (Compound 1024)

Ortho-phenylenediamine [1.08 gm., 0.01 mole] and 1,6-di($N^3$-cyano-N'-guanidino) hexane [1.25 gm., 0.005 mole] were finely ground in a mortar and pestle. The intimate mix was refluxed with water [10 ml] and concentrated hydrochloric acid [2.0 ml] for 2 hours. The reaction mixture was allowed to cool to room temperature and the pinkish solid filtered and air dried. This solid was stirred at room temperature with ether, then filtered and air dried. This material was rewashed with water till no more color was removed, then washed with ether, air dried, and finally dried over boiling xylene and under vacuum to give an off-white solid which melted at 170°–174° C.

| Analysis: | C | H | Cl | N |
|---|---|---|---|---|
| Calculated for $C_{22}H_{28}N_{10} \cdot 2HCl \cdot 1\frac{1}{2} H_2O$ | 49.62 | 6.20 | 13.34 | 26.32 |
| Found: | 49.28 | 6.19 | 12.97 | 26.57 |

EXAMPLE 4

N'-N''-bis-[2-(5'-chloro-6'-sulfamyl benzimidazole)]-2,9-diazadecane diimidamide dihydrochloride (Compound 1045)

4-Chloro-5-sulfamyl-o-phenylene diamine [12.1 gm., 0.55 mole] and 1,6-di ($N^3$-cyano-N'-guanidino) hexane [6.9 gm., 0.0275 mole] were finely ground in a mortar and pestle. The intimate mix was refluxed with water [55 ml] and concentrated hydrochloric acid [11.0 ml] for 4 hours. The solution was allowed to cool to room temperature overnight. The brown solid was filtered, washed with water, and air dried. The solid was then washed with ethanol, then ether, air dried, then dried over boiling xylene and under vacuum for 3 hours. The grey solid [3.8 gm] had melting point of 200°–210° C. with decomposition.

| Analysis: | C | H | Cl | N | S |
|---|---|---|---|---|---|
| Calculated for $C_{22}H_{28}Cl_2N_{12}O_4S_2 \cdot 2HCl \cdot 3H_2O$ | 33.59 | 4.58 | 18.07 | 21.37 | 8.14 |
| Found: | 33.97 | 4.24 | 17.56 | 21.37 | 8.81 |

EXAMPLE 5

N'-N''-bis-[2-benzimidazole]-2,10-diazaundecane diimidamide dihydrochloride (Compound 1046)

Ortho-phenylene diamine [5.4 gm., 0.05 mole] and 1,7-di($N^3$-cyano-N'-quanidino)heptane [6.6 gm., 0.025 mole] were finely ground in a pestle and mortar. The intimate mix was refluxed with water [50 ml] and concentrated hydrochloric acid [10.0 ml] for 3 hours. The solution was allowed to cool to room temperature and the pinkish solid was filtered and air dried. The solid was washed with ether, dissolved in methanol filtered to remove a small amount of particulate, and the methanol evaporated to dryness to give a brown oil. On trituration with ether, the oil solidified as a brown solid. This solid was dried under vacuum at room temperature for 5 hours. The brown solid [2.0 gm] had melting point of 104°–109° C. with decomposition.

| Analysis: | C | H | Cl | N |
|---|---|---|---|---|
| Calculated for $C_{23}H_{30}N_{10} \cdot 2HCl \cdot 3H_2O$ | 48.16 | 6.63 | 12.39 | 24.43 |
| Found: | 48.31 | 6.31 | 12.52 | 24.24 |

EXAMPLE 6

N'-N''-bis-[2-benzimidazole]-2,7-diazaoctane diimidamide dihydrochloride

Ortho-phenylenediamine [5.4 gm., 0.05 mole] and 1,4-di($N^3$-cyano-N' guanidino) butane [5.56 gm., 0.025 mole] were finely ground in a mortar and pestle. The intimate mix was refluxed with water [50 ml] and concentrated hydrochloric acid [10 ml] for 3 hours. The solution was allowed to cool at room temperature and the beige solid was filtered and air dried. This solid was repeatedly triturated with ethanol until no more color was removed, then triturated with ether and air dried. The greyish solid was dried under vacuum at room temperature for 5 hours. The grey solid [400 mg] had melting point of 148°–154° C.

| Analysis: | C | H | Cl | N |
|---|---|---|---|---|
| Calculated for $C_{20}H_{24}N_{10} \cdot 2HCl \cdot 3\frac{1}{2} H_2O$ | 44.44 | 6.11 | 13.15 | 25.93 |
| Found | 44.43 | 6.06 | 13.39 | 26.04 |

EXAMPLE 7

N'-N''-bis[2-benzimidazole]-2,5-diazahexane diimidamide dihydrochloride (Compound 1069)

Ortho-phenylenediamine [10.8 gm., 0.1 mole] and 1,2-di($N^3$-cyano-N'-guanidino) ethane [9.7 gm., 0.05 mole] were finely ground in a pestle and mortar. The intimate mix was refluxed with 2N hydrochloric acid [120 ml] for 2 hours. The solution was allowed to cool to room temperature and the pink solid was filtered and air dried. The solid was washed with water, then ethanol until no more color was removed. The beige solid was then dried under facuum and over boiling toluene for 6 hours. The beige solid [5.4 gm] had melting point of 94°–99° C.

| Analysis: | C | H | Cl | N |
|---|---|---|---|---|
| Calculated for $C_{18}H_{20}N_{10} \cdot 2HCl \cdot 3\frac{1}{2} H_2O$: | 42.18 | 5.66 | 13.86 | 27.34 |
| Found: | 41.50 | 5.39 | 13.73 | 27.91 |

EXAMPLE 8

N'-N''-bis-[2-(6-nitrobenximidazole)]-2,5-diazahexane diimidamide dihydrochloride 4-Nitro-o-phenylenediamine [15.3 gm., 0.1 mole] and 1,2-di($N^3$-cyano-N'-guanidino) ethane [9.7 gm., 0.05 mole] were finely ground in a pestle and mortar. The intimate mix was refluxed with 2N hydrochloric acid [120 ml] for 2 hours. The solution was allowed to cool to room temperature and the greenish solid was filtered and air dried. The solid was triturated with water, then ethanol until no more color was removed. The light green solid was dried under vacuum and over boiling toluene for 4 hours. The green solid [4.3 gm] had melting point of 207°–211° C.

| Analysis: | C | H | Cl | N |
|---|---|---|---|---|
| Calculated for $C_{18}H_{18}N_{12}O_4$ 2HCl 2$H_2O$ | 37.56 | 4.47 | 12.35 | 29.22 |
| Found: | 37.52 | 4.03 | 12.08 | 29.55 |

EXAMPLE 9

N'-N''-bis-[2-benzimidazole]-2,6-diazaheptane diimidamide dihydrochloride trihydrate Ortho-phenylenediamine [5.4 gm., 0.05 mole] and 1,3-di($N^3$-cyano-$N^1$-guanidino) propane [5.2 gm., 0.025 mole] were finely ground in a pestle and mortar. The intimate mix was refluxed with 2N hydrochloric acid [60 ml] for 3 hours. The solution was allowed to cool to room temperature. The pinkish solid was filtered, washed with a little water, and air dried. The solid was washed with ether till no more color was removed. The pinkish solid was air dried, then dried under vacuum at room temperature for 6 hours. The pink solid [700 mg.] had melting point of 120°–126° C.

| Analysis | C | H | Cl | N |
|---|---|---|---|---|
| Calculated for $C_{19}H_{22}N_{10}$ 2HCl 3$H_2O$ | 44.10 | 5.80 | 13.73 | 27.80 |
| Found: | 43.67 | 5.53 | 13.58 | 27.52 |

EXAMPLE 10

N'-N''-bis-[2-(6-nitro benzimidazole]-2,10-diazaundecane diimidamide dihydrochloride dihydrate 4-Nitro-o-phenylene diamine [15.3 gm., 0.1 mole] and 1,7 di-($N^3$-cyano-$N^1$-guandidino) heptane [13.2 gm., 0.05 mole] were finely ground in a mortar and pestle. The intimate mix was refluxed with 2N hydrochloric acid [100 ml] for 3 hours. The reaction mixture was allowed to cool to room temperature. The solid was filtered and air dried, washed with a little water and then with ethanol till no more color was removed. The green solid was triturated with ether several times and then dried under vacuum and over boiling xylene for 6 hours. The green solid [2.1 gm] had a melting point of 165°–172° C.

| Analysis: | C | H | Cl | N |
|---|---|---|---|---|
| Calculated for $C_{23}H_{28}N_{12}O_4$·2HCl·2$H_2O$ | 42.79 | 5.27 | 11.01 | 26.05 |
| Found: | 42.52 | 5.00 | 10.67 | 25.99 |

EXAMPLE 11

N'-N''-bis-[2-(6-methylbenzimidazole)]-2,5-diazahexane diimidamide dihydrochloride monohydrate (Compound 1072)

4-methyl-o-phenylene diamine [12.2 gm., 0.1 mole] and 1,2-di($N^3$-cyano-$N^1$-guanidino) ethane [9.7 gm., 0.05 mole] were finely ground in a mortar and pestle. The intimate mix was refluxed with 2N hydrochloric acid [120 ml] for 2 hours. The solution was allowed to cool to room temperature. The pinkish solid was filtered, washed with a little water and air dried. The solid was washed with ether until no more color was removed. The light grey solid was air dried, and then dried under vacuum and over boiling toluene for 4 hours. The light grey solid [2.9 gm.] had a melting point of 182°–188° C.

| Analysis: | C | H | Cl | N |
|---|---|---|---|---|
| Calculated for $C_{20}H_{24}N_{10}$·2HCl·$H_2O$ | 48.49 | 5.66 | 14.34 | 28.28 |
| Found: | 48.11 | 5.59 | 14.75 | 28.50 |

EXAMPLE 12

N'-N''-bis-[2-(6-nirtobenzimidazole)]-2,8-diazanonane diimidamide dihydrochloride hemipentahydrate 4-nitro-o-phenylene diamine[;2/24 g,., 0.08 mole] and 1,5-di($N^3$-cyano-N'-guanidino) pentane [9.44 gm., 0.04 mole] were finely ground in a mortar and pestle. The intimate mix was refluxed with 2N hydrochloric acid [96 ml] for 3 hours. The solution was allowed to cool to room temperature. The brownish solid was filtered off and air dried. The solid was washed with ethanol till no more color was removed. The light green solid was air dried, then dried under vacuum and over boiling toluene for 6 hours. The green solid [6.6 gm.] had a melting point of 205°–210° C.

| Analysis: | C | H | Cl | N |
|---|---|---|---|---|
| Calculated for $C_{21}H_{24}N_{12}O_4$ 2HCl 2½ $H_2O$ | 40.26 | 4.95 | 11.34 | 26.83 |
| Found: | 39.81 | 4.32 | 11.76 | 26.96 |

EXAMPLE 13

N'-N''-bis-[2-(6-methylbenzimidazole)]-2,8-diazanonane diimidamide dihydrochloride hemipentahydrate (Compound 1074)

4-methyl-o-phenylene diamine [9.76 gm., 0.08 mole] and 1,5-di($N^3$-cyano-N'-guanidino) pentane [9.44 gm., 0.04 mole] were finely ground in a mortar and pestle. The intimate mix was refluxed with 2N hydrochloric acid [96 ml] for 3 hours. The solution was allowed to cool to room temperature. The light grey solid was filtered from the reaction mixture and air dried. The solid was then washed with ethanol until no more color was removed. The light grey solid was air dried, and then dried under vacuum at room temperature for 5 hours. The solid [6.2 gm.] had a melting point of 76°–81° C.

| Analysis: | C | H | Cl | N |
|---|---|---|---|---|
| Calculated for | | | | |
| $C_{23}H_{30}H_{10}$.2HCl 2½ $H_2O$: | 48.93 | 6.56 | 12.59 | 24.82 |
| Found | 49.08 | 6.60 | 12.93 | 25.18 |

EXAMPLE 14

N'-N''-bis-[2-(6-chlorobenzimidazole)]-2,8,diazanonane diimidamide dihydrochloride hydrate (Compound 1075)

4-chloro-o-phenylene diamine [11.4 gm., 0.08 mole] and 1,5-di($N^3$-cyano-$N^1$-guanidino) pentane [9.44 gm., 0.04 mole] were finely ground in a pestle and mortar. The intimate mix was refluxed with 2N hydrochloric acid [96 ml] for 3 hours. The solution was allowed to cool to room temperature. The black solid was filtered and air dried. The solid was then washed with ether till no more color was removed. The grey solid was air dried, then dried, under vacuum at room temperature for 5 hours. The grey solid [8.7 gm.] had a melting point 138°–145° C.

| Analysis: | C | H | Cl | N |
|---|---|---|---|---|
| Calculated for | | | | |
| $C_{21}H_{24}Cl_2N_{10}$ 2HCl 2$H_2O$: | 42.28 | 5.03 | 23.83 | 23.49 |
| Found: | 42.15 | 5.12 | 23.93 | 23.29 |

EXAMPLE 15

N'-N''-bis-[2-(6-nitrobenzimidazole)]=2,6-diazaheptane diimidamide dihydrochloride hemihydrate 4-nitro-o-phenylene diamine [7.65 gm., 0.05 mole] and 1,3-di($N^3$-cyano-N'-guandino)propane[5.2 gm., 0.025 mole] were finely ground in a mortar and pestle. The intimate mix was refluxed with 2N hydrochloric acid [60 ml] for 3 hours. The solution was allowed to cool to room temperature. The yellowish solid was filtered from the reaction mixture and air dried. The solid was washed with ethanol till no more color was removed. The yellow solid was air dried, then dried under vacuum and over boiling toluene for 8 hours. The yellow solid [2.9 gm.] had a melting point of 263°–267° C.

| Analysis: | C | H | Cl | N |
|---|---|---|---|---|
| Calculated for | | | | |
| $C_{19}H_{20}N_{12}O_4$ 2HCl ½ $H_2O$ | 40.57 | 4.09 | 12.63 | 29.89 |
| Found: | 40.46 | 4.33 | 13.04 | 30.07 |

EXAMPLE 16

N'-N''-bis[2-(6-nitro benzimidazole)]-2,11-diazadodecane diimidamide dihydrochloride hemipentahydrate 4-Nitro-o-phenylene diamine [7.65 gm., 0.05 mole] and 1,8 di-($N^3$-cyano-$N^1$-guanidino) octane[6.95 gm., 0.025 mole] were finely ground in a mortar and pestle. The intimate mix was refluxed with 2N hydrochloric acid [60 ml] for 2 hours. The reaction mixture was allowed to cool to room temperature. The solid was filtered and air dried, washed with a little water then with ethanol till no more color was removed. The green solid was triturated with ether several times then dried under vacuum and over boiling xylene for 6 hours. The green solid [6.1 gm.] had a melting point of 158°–165° C.

| Analysis: | C | H | Cl | N |
|---|---|---|---|---|
| Calculated for | | | | |
| $C_{24}H_{30}N_{12}O_4$12HCl.2½ $H_2O$ | 43.11 | 5.54 | 10.63 | 25.15 |
| Found | 43.09 | 5.55 | 10.80 | 25.44 |

EXAMPLE 17

N'-N''-bis-[2-(6-chloro benzimidazole)]-2,6-diazaheptane diimidamide dihydrochloride dihydrate 4-Chloro-phenylene diamine [7.12 gm., 0.05 mole] and 1,3di-($N^3$-cyano-$N^1$-guanidino) propane [5.2 gm., 0.025 mole] were finely ground in a mortar and pestle. The intimate mix was refluxed with 2N hydrochloric acid [60 ml] for 2 hours. The reaction mixture was allowed to cool to room temperature. The solid was filtered and air dried, washed with a little water and then with ethanol till no more color was removed. The grey solid was triturated with ether several times, then dried under vacuum and over boiling xylene for 4 hours. The grey solid [4.5 gm.] had a melting point of 95°–100° C.

| Analysis: | C | H | Cl | N |
|---|---|---|---|---|
| Calculated for | | | | |
| $C_{19}H_{20}Cl_2N_{10}$.2HCl.2$H_2O$ | 40.14 | 4.58 | 25.00 | 24.65 |
| Found: | 40.01 | 4.73 | 25.37 | 24.36 |

EXAMPLE 18

N-N''-bis=[2-(6-methyl benzimidazole)]-2,11-diazadodecane diimidamide dihydrochloride sesquihydrate 4-Methyl-o-phenylene diamine [6.1 gm., 0.025 mole] were finely ground in a mortar and pestle. The intimate mix was refluxed with 2N hydrochloric acid [60 ml] for 2 hours. The reaction mixture was allowed to cool to room temperature. The solid was filtered and air dried, washed with a little water then with ethanol till no more color was removed. The white solid was triturated with ether several times then dried under vacuum and over boiling xylene for 5 hours. The white solid [2.9 gm.] had a melting point of 155°–160° C.

| Analysis: | C | H | Cl | N |
|---|---|---|---|---|
| Calculated for | | | | |
| $C_{26}H_{36}N_{10}$.2HCl.1½ $H_2O$ | 53.06 | 6.97 | 12.07 | 23.81 |
| Found: | 52.31 | 6.76 | 12.38 | 24.10 |

EXAMPLE 19

N'-N''-bis-[2-(6-chloro benzimidazole)]-2,7-diazaoctane diimidamide dihydrochloride sesquihydrate 4-Chloro-o-phenylenediamine [7.13 gm., 0.05 mole] and 1,4 di-($N^3$-cyano-$N^1$-guanidino) butane [5.55 gm., 0.025 mole] were finely ground in a mortar and pestle. The intimate mix was refluxed with 2N hydrochloric acid [60 ml] for 2 hours. The reaction mixture was allowed to cool to room temperature. The solid was filtered and air dried, washed with a little water then with ethanol till no more color was removed. The grey solid was triturated with ether several times then dried under vacuum and over boiling xylene for 4 hours. The grey solid [3.6 gm.] had a melting point of 168°–175° C.

| Analysis: | C | H | Cl | N |
|---|---|---|---|---|
| Calculated for | | | | |
| $C_{20}H_{22}Cl_2N_{10}.2HCl.1\frac{1}{2} H_2O$ | 41.88 | 4.71 | 24.78 | 24.43 |
| Found: | 41.83 | 4.29 | 24.28 | 24.39 |

EXAMPLE 20

N'-N''-bis-[2-(6-carboxy benzimidazole)]-2,9-diazadecane diimidamide dihydrochloride sesquihydrate 3,4-Diamino benzoic acid [15.2 gm., 0.1 mole] and 1,6 di-($N^3$-cyano-$N^1$-guanidino) hexane [12.5 gm., 0.05 mole] were finely ground in a mortar and pestle. The intimate mix was refluxed with 2N hydrochloric acid [120 ml] for 4 hours. The reaction mixture was allowed to cool to room temperature. The solid was filtered and air dried, washed with a little water then with ethanol till no more color was removed. The off-white solid was triturated with ether several times then dried under vacuum and over boiling xylene for 5 hours. The off-white solid [7.5 gm.] had a melting point of 231°–237° C.

| Analysis: | C | H | Cl | N |
|---|---|---|---|---|
| Calculated for | | | | |
| $C_{24}H_{28}N_{10}O_4.2HCl.1\frac{1}{2} 2H_2O$ | 46.45 | 5.32 | 11.45 | 22.58 |
| Found: | 46.55 | 5.46 | 11.85 | 22.75 |

EXAMPLE 21

N'-N''-bis-[2-(6-methyl-benzimidazole)]-2,9-diazadecane diimidamide dihydrochloride dihydrate (Compound 1081)

4-methyl-o-phenylenediamine [6.1 gm., 0.05 mole] and 1,6 di-($N^3$-cyano-$N^1$-guanidino) hexan [6.25 gm., 0.025 mole] were finely ground in a mortar and pestle. The intimate mix was refluxed with 2N hydrochloric acid [60 ml] for 2 hours. The reaction mixture was allowed to cool to room temperature. The solid was filtered and air dried, washed with a little ethanol till no more color was removed. The off-white solid was triturated with ether several times and then dried under vacuum and over boiling xylene for 5 hours. The beige solid [4.4 gm.] had a melting point of 156°–162° C.

| Analysis: | C | H | Cl | N |
|---|---|---|---|---|
| Calculated for | | | | |
| $C_{24}H_{32}N_{10}.2HCl.2H_2O$ | 50.62 | 6.68 | 12.48 | 24.61 |
| Found: | 50.59 | 6.29 | 13.15 | 24.79 |

EXAMPLE 22

N'-N''-bis-[2-benzimidazole]-2,11-diazadodecane diimidamide dihydrochloride dihydrate (Compound 1080)

Ortho-phenylenediamine [5.4 gm., 0.05 mole] and 1.8 di-($N^3$-cyano-$N^1$-guanidino) octane [6.95 gm., 0.025 mole] were finely ground in a mortar and pestle. The intimate mix was refluxed with 2N hydrochloric acid [50 ml] for 2 hours. The reaction mixture was allowed to cool to room temperature. The solid was filtered and air dried, washed with a little water and then with ethanol till no more color was removed. The pinkish solid was triturated with ether several times, then dried under vacuum and over boiling xylene for 4 hours. The beige solid [3.6 gm.] had a melting point of 132°–138° C.

| Analysis: | C | H | Cl | N |
|---|---|---|---|---|
| Calculated for | | | | |
| $C_{24}H_{32}N_{10}.2HCl.2H_2O$ | 50.62 | 6.68 | 13.48 | 24.60 |
| Found: | 50.44 | 7.04 | 13.28 | 24.34 |

EXAMPLE 23

N'-N''-bis-[2-benzimidazole]-2,8-diazanonane diimidamide dihydrochloride dihydrate (Compound 1079)

Ortho-phenylenediamine [8.64 gm., 0.08 mole] and 1.5 di-($N^3$-cyano-$N^1$-guanidino) pentane [9.44 gm., 0.04 mole] were finely ground in a mortar and pestle. The intimate mix was refluxed with 2N hydrochloric acid [96 ml] for 3 hours. The reaction mixture was allowed to cool to room temperature. The solid was filtered and air dried, washed with a little water and then with ethanol till no more color was removed. The pinkish solid was triturated with ether several times, then dried under vacuum and over boiling xylene for 6 hours. The pinkish solid [5.8 gm.] had a melting point of 116°–121° C.

| Analysis: | C | H | Cl | N |
|---|---|---|---|---|
| Calculated for | | | | |
| $C_{21}H_{26}N_{10}.2HCl.2H_2O$ | 47.81 | 6.07 | 13.47 | 26.57 |
| Found | 48.17 | 5.89 | 13.65 | 26.80 |

EXAMPLE 24

N'-N''-bis-[2-(6-methyl benzimidazole)]-2,12-diazatridecane diimidamide dihydrochloride sesquihydrate 4-Methyl-o-phenylene diamine [6.1 gm., 0.05 mole] and 1,9 di-($N^3$-cyano-$N^1$-guanidino] nonane [7.3 gm., 0.025 mole] were finely ground in a mortar and pestle. The intimate mix was refluxed with 2N hydrochloric acid [55 ml.] for 2 hours. The reaction mixture was allowed to cool to room temperature. The solid was filtered and air dried, washed with a little water, then with ethanol till no more color was removed. The off-white solid was triturated with ether several times, then dried under vacuum and over boiling xylene for 5 hours. The beige solid [1.2 gm.] had a melting point of 152°–156° C.

| Analysis: | C | H | Cl | N |
|---|---|---|---|---|
| Calculated for | | | | |
| $C_{27}H_{38}N_{10}.2HCl.1\frac{1}{2} H_2O$ | 53.82 | 7.14 | 11.79 | 23.26 |
| Found: | 53.61 | 7.23 | 12.06 | 23.37 |

EXAMPLE 25

N'-N''-bis-[2-(6-methyl benzimidazole)]-2,7-diazaoctane diimidamide dihydrochloride dihydrate 4-Methyl-o-phenylene diamine [6.1 gm., 0.05 mole] and 1,4 di-($N^3$-cyano-$N^1$-guanidino) butane [5.55 gm., 0.024 mole] were finely ground in a mortar and pestle. The intimate mix was refluxed with 2N hydrochloric acid [60 ml.] for 2 hours. The reaction mixture was allowed to cool to room temperature. The solid was filtered and air dried, washed with a little water then with ethanol till no more color was removed. The off-white solid was triturated with ether several times, then dried under vacuum and over boiling xylene for 5 hours. The beige solid [1.2 gm.] had a melting point of 160°–166° C.

| Analysis: | C | H | Cl | N |
|---|---|---|---|---|
| Calculated for $C_{22}H_{28}N_{10}.2HCl.2H_2O$ | 48.79 | 6.28 | 13.13 | 25.88 |
| Found | 48.84 | 5.89 | 13.81 | 26.58 |

EXAMPLE 26

N'-N''-bis-[2-(6-chloro benzimidazole)]-2,11-diazadodecane diimidamide dihydrochloride sesquihydrate 4-Chloro-o-phenylene diamine [7.13 gm., 0.05 mole] and 1.8 di($N^3$-cyano-$N^1$-guanidino)octane [6.95 gm., 0.025 mole] were finely ground in a mortar and pestle. The intimate mix was refluxed with 2Nhydrochloric acid [60 ml] for 2 hours. The reaction mixture was allowed to cool to room temperature. The solid was filtered and air dried, washed with a little water and then with ethanol till no more color was removed. The grey solid was triturated with ether several times, then dried under vacuum and over boiling xylene for 5 hours. The grey solid [5.7 gm.] had a melting point of 175°–180° C.

| Analysis: | C | H | Cl | N |
|---|---|---|---|---|
| Calculated for $C_{24}H_{30}Cl_2N_{10}.2HCl.1\frac{1}{2}H_2O$ | 45.79 | 5.56 | 22.58 | 22.26 |
| Found: | 45.47 | 5.36 | 22.83 | 22.29 |

EXAMPLE 27

N'-N''-bis-[2-(6-methyl benzimidazole)]-2,6-diazaheptane diimidamide dihydrochloride monohydrate 4-methyl-o-phenylene diamine [6.1 gm., 0.05 mole] and 1.3 di-($N^3$-cyano-$N^1$-guanidino) propane [5.2 gm., 0.025 mole] were finely ground in a mortar and pestle. The intimate mix was refluxed with 2N hydrochloric acid [60 ml] for 3 hours. The reaction mixture was allowed to cool to room temperature. The solid was filtered and air dried, washed with a little water and then with ethanol till no more color was removed. The white solid was triturated with ether several times, then dried under vacuum and over boiling xylene for 4 hours. The white solid [3.0 gm.] had a melting point of 170°–174° C.

| Analysis: | C | H | Cl | N |
|---|---|---|---|---|
| Calculated for $C_{21}H_{26}N_{10}.2HC.1H_2O$ | 49.50 | 5.89 | 13.95 | 27.51 |
| Found: | 49.80 | 5.71 | 14.32 | 27.04 |

EXAMPLE 28

N'-N''-bis-[2-(6-nitro benzimidazole)]-2,7-diazaoctane diimidamide dihydrochloride monohydrate 4-Nitro-o-phenylene diamine [7.65 gm., 0.05 mole] and 1.4 di-($N^3$-cyano-$N^1$-guanidino)butane [5.55 gm., 0.025 mole] were finely ground in a mortar and pestle. The intimate mix was refluxed with 2N hydrochloric acid [60 ml] for 2 hours. The reaction mixture was allowed to cool to room temperature. The solid was filtered and air dried, washed with a little water and then with ethanol till no more color was removed. The green solid was triturated with ether several times, then dried under vacuum and over boiling xylene for 5 hours. The green solid [3.6 gm.] had a melting point of 244°–251° C.

| Analysis: | C | H | Cl | N |
|---|---|---|---|---|
| Calculated for $C_{20}H_{22}N_{12}O_4.2HCl.H_2O$ | 41.03 | 4.44 | 12.14 | 28.71 |
| Found: | 40.74 | 4.45 | 12.58 | 28.47 |

EXAMPLE 29

N'-N''-bis-[2-(6-chloro benzimidazole)]-2,13-diazatetradecane diimidamide dyhydrochloride monohydrate 4-Chloro-o-phenylene diamine [14.3 gm., 0.1 mole] and 1,10 di-($N^3$-cyano-$N^1$-guanidino) decane [15.3 gm., 0.05 mole] were finely ground in a mortar and pestle. The intimate mix was refluxed with 2N hydrochloric acid [120 ml] for 3 hours. The reaction mixture was allowed to cool to room temperature. The solid was filtered and air dried, washed with a little water and then with ethanol till no more color was removed. The grey solid was triturated with ether several times, then dried under vacuum and over boiling xylene for 6 hours. The grey solid [10.4 gm.] had a melting point of 164°–170° C.

EXAMPLE 30

N'-N''-bis-[2-(6-methyl benzimidazole)]-2,10-diazaundecane diimidamide dihydrochloride hemipentahydrate 4-Methyl-o-phenylene diamine [12.2 gm., 0.1 mole] and 1,7 di-$N^3$-cyano-$N^1$-guanidino) heptane [13.2 gm., 0.05 mole] were finely ground in a mortar and pestle. The intimate mix was refluxed with 2N hydrochloric acid [100 ml] for 3 hours. The reaction mixture was allowed to cool to room temperature. The solid was filtered and air dried, washed with a little water then with ethanol till no more color was removed. The beige solid was triturated with ether several times then dried under vacuum for 8 hours. The beige solid [14.9 gm.] had a melting point of 92°–96° C.

| Analysis | C | H | Cl | N |
|---|---|---|---|---|
| Calculated for | | | | |

| Analysis | C | H | Cl | N |
|---|---|---|---|---|
| $C_{25}H_{34}N_{10}\cdot 2HCl\cdot 2\frac{1}{2} H_2O$ | 50.67 | 6.93 | 11.99 | 23.64 |
| Found: | 50.02 | 6.63 | 12.43 | 24.01 |

EXAMPLE 31

N'-N''-bis-[2-(6-Chloro benzimidazole)]-2,10-diazaundecane diimidamide dihydrochloride monohydrate 4-Chloro-o-phenylene diamine [14.5 gm., 0.1 mole] and 1,7 di-($N^3$-cyano-$N^1$-guanidino)heptane [13.2 gm., 0.05 mole] were finely ground in a mortar and pestle. The intimate mix was refluxed with 2N hydrochloric acid [100 ml] for 3 hours. The reaction mixture was allowed to cool to room temperature. The solid was filtered and air dried, washed with a little water then with ethanol till no more color was removed. The grey solid was triturated with ether several times then dried under vacuum and over boiling xylene for 8 hours. The grey solid [12.3 gm.] had a melting point of 168°–176° C.

| Analysis: | C | H | Cl | N |
|---|---|---|---|---|
| Calculated for $C_{23}H_{28}Cl_2N_{10}\cdot 2HCl\cdot H_2O$ | 45.55 | 5.28 | 23.43 | 23.10 |
| Found: | 45.75 | 5.42 | 23.32 | 23.05 |

EXAMPLE 32

N'-N''-bis-[2-(6-nitro benzimidazole)]-2,12-diazatridecane diimidamide dihydrochloride monohydrate 4-Nitro-o-phenylene diamine [7.65 gm., 0.05 mole] and 1,9 di-($N^3$-cyano-$N^1$-guanidino) nonane [7,3 gm., 0.025 mole] were finely ground in a mortar and pestle. The intimate mix was refluxed with 2N hydrochloric acid [55 ml] for 3 hours. The reaction mixture was allowed to cool to room temperature. The solid was filtered and air dried, washed with a little water and then with ethanol till no more color was removed. The green solid was triturated with ether several times, then dried under vacuum and over boiling xylene for 4 hours. The green solid [4.3 gm.] had a melting point of 150°–157° C.

| Analysis: | C | H | Cl | N |
|---|---|---|---|---|
| Calculated for $C_{25}H_{32}N_{12}O_4\cdot 2HCl\cdot H_2O$ | 45.80 | 5.50 | 10.84 | 25.65 |
| Found: | 45.77 | 5.68 | 10.74 | 26.14 |

EXAMPLE 33

N'-N''-bis-[2-(6-chloro benzimidazole)]-2,5-diazahexanediimidamide dihydrochloride sesquihydrate (Compound 1105)

4-Chloro-o-phenylene diamine [10.7 gm., 0.075 mole] and 1,2 di-($N^3$-cyano-$N^1$-guanidino)ethane [7.3 gm., 0.037 mole] were finely ground in a mortar and pestle. The intimate mix was refluxed with 2N hydrochloric acid [90 ml] for 3 hours. The reaction mixture was allowed to cool to room temperature. The solid was filtered and air dried, washed with a little water and then with ethanol till no more color was removed. The grey solid was triturated with ether several times, then dried under vacuum and over boiling xylene for 6 hours. The grey solid [4.9 gm.] had a melting point of 182°–188° C.

| Analysis: | C | H | Cl | N |
|---|---|---|---|---|
| Calculated for $C_{18}H_{18}Cl_2N_{10}\cdot 2HCl\cdot 1\frac{1}{2} H_2O$ | 39.63 | 4.22 | 26.06 | 25.69 |
| Found | 39.06 | 4.10 | 26.16 | 26.10 |

EXAMPLE 34

N'-N''-bis-[2-(6-chloro benzimidazole)]-2,12-diazatridecane diimidamide dihydrochloride monohydrate 4-Chloro-o-phenylene diamine [7.13 gm., 0.05 mole] and 1.0 di-($N^3$-cyano-$N^1$=guanidino) nonane [7.3 gm., 0.025 mole] were finely ground in a mortar and pestle. The intimate mix was refluxed with 2N hydrochloric acid [55 ml] for 2 hours. The reaction mixture was allowed to cool to room temperature. The solid was filtered and air dried, washed with a little water and then with ethanol till no more color was removed. The grey solid was triturated with ether several times, then dried under vacuum and over boiling xylene for 5 hours. The grey solid [1.4 gm.] had a melting point of 154°–158° C.

| Analysis: | C | H | Cl | N |
|---|---|---|---|---|
| Calculated for $C_{25}H_{32}Cl_2N_{10}\cdot 2HCl\cdot H_2O$ | 47.32 | 5.68 | 22.08 | 22.40 |
| Found: | 47.24 | 5.85 | 21.47 | 22.66 |

EXAMPLE 35

N'-N''-bis-[2-(6-methyl benzimidazole)]-2,13-diazatetradecane diimidamide dihydrochloride sesquihydrate 4-Methyl-o-phenylene diamine [6.1 gm., 0.05 mole] and 1,10 di-($N^3$-cyano-$N^1$-guanidino) decane [7.65 gm., 0.025 mole] were finely ground in a mortar and pestle. The intimate mix was refluxed with 2N hydrochloric acid [60 ml] for 3 hours. The reaction mixture was allowed to cool to room temperature. The solid was filtered and air dried, washed with a little water and then with ethanol till no more color was removed. The white solid was triturated with ether several times, then dried under vacuum and over boiling xylene for 4 hours. The white solid [3.8 gm.] had a melting point of 140°–148° C.

| Analysis: | C | H | Cl | N |
|---|---|---|---|---|
| Calculated for $C_{28}H_{40}N_{10}\cdot 2HCl\cdot 1\frac{1}{2} H_2O$ | 54.54 | 7.31 | 11.53 | 22.72 |
| Found: | 54.38 | 7.33 | 11.66 | 23.28 |

EXAMPLE 36

N'-N''-bis-[2-benzimidazole]-2,13-diazatetradecane diimidamide dihydrochloride sesquihydrate Ortho-phenylene diamine [10.8 gm., 0.1 mole] and 1,10 di-($N^3$-cyano-$N^1$-guanidino) decene [15.3 gm., 0.05 mole] were finely ground in a mortar and pestle. The intimate mix was refluxed with 2N hydrochloric acid [120 ml] for 6 hours. The reaction mixture was allowed to cool to room temperature. The solid was filtered and air dried, washed with a little water and then with ethanol till no more color was removed. The white solid was triturated with ether several times, then dried under vacuum and over boiling xylene for 5 hours. The white solid [2.5 gm.] had a melting point of 96°–105° C.

| Analysis: | C | H | Cl | N |
|---|---|---|---|---|
| Calculated for | | | | |
| $C_{26}H_{36}N_{10}.2HCl.1\frac{1}{2} H_2O$ | 53.06 | 6.97 | 12.07 | 23.81 |
| Found: | 52.84 | 7.17 | 12.38 | 24.56 |

The following compounds are produced in similar manner:

N'-N''-bis-[2-(6-chlorobenzimidazole)]2,5-diazahexane diimidamide di HCl.

N'-N''-bis-[2-(6methylbenzimidazole)]-2,5-diazahexane diimidamide di HCl.

N'-N''-bis[2-(5,6-dimethylbenzimidazole)]-2,5-diazahexane diimidamide di HCl.

N'-N''-bis[2-(5,6-dichlorobenzimidazole)]=2,5-diazahexane diimidamide di HCl.

N'-N''-bis[2-(6-carboxylbenzimidazole)]-2,5-diazahexane diimidamide di HCl.

N'-N''-bis[2-(6-methoxybenzimidazole)]-2,5-diazahexane diimidamide di HCl.

N'-N''-bis-[2-benzimidazole]-2,6-diazaheptane diimidamide di HCl.

N'-N''-bis[2-(6-chlorobenzimidazole)]-2,6-diazaheptane diimidamide di HCl.

N'-N''-bis[2-(6-nitrobenzimidazole)]-2,6-diazaheptane diimidamide di HCl.

N'-N''-bis[2-(6-methylbenzimidazole)]-2,6-diazaheptane diimidamide di HCl.

N'-N''-bis[2-(6-methoxybenzimidazole)]-2,6-diazaheptane diimidamide di HCl.

N'-N''-bis[2-(6-carboxybenzimidazole)]-2,6-diazaheptane diimidamide di HCl.

N'-N''-bis-[2-(5,6-dichlorobenzimidazole)]2,6-diazaheptane diimidamide di HCl.

N'-N''-bis-[2-(5,6-dimethylbenzimidazole)]2,6-diazaheptane diimidamide di HCl.

N'-N''-bis-[2-benzimidazole]-2,7-diazaoctane diimidamide di HCl.

N'-N''-bis-[2-(6-chlorobenzimidazole)-]-2,7-diazaoctane diimidamide di HCl.

N'-N''-bis-[2-(6-methylbenzimidazole)]-2,7-diazaoctane diimidamide di HCl.

N'-N''-bis-[2-(6-nitrobenzimidazole)]-2,7-diazaoctane diimidamide di HCl.

N'-N''-bis-[2-(5,6-dimethylbenzimidazole)]-2,7-diazaoctane diimidamide di HCl.

N'-N''-bis-[2-(5,6-dichlorobenzimidazole)]-2,7-diazaoctane diimidamide di HCl.

N'-N''-bis-[2-(6-carboxybenzimidazole)]-2,7-diazaoctane diimidamide di HCl.

N'-N''-bix-[2-(6-methoxybenzimidazole)]-2,7-diazaoctane diimidamide di HCl.

N'-N''-bis-[2-benzimidazole]-2,8-diazanonane diimidamide di HCl.

N'-N''-bis[2-(6-chlorobenzimidazole)-2,8-diazanonane diimidamide di HCl.

N'-N''-bis[2-(6-methylbenximidazole]-2,8-diazononane diimidamide di HCl.

N'-N''-bis[2-(6-nitrobenzimidazole)]-2,8-diazanonane diimidamide di HCl.

N'-N''-bis[2-(5,6-dimethylbenzimidazole)]2,8-diazanonane diimidamide di HCl.

N'-N''-bis[2-(5,6-dichlorobenzimidazole)]2,8-diazanonane diimidamide di HCl.

N'-N''-bis[2-(6-carboxybenzimidazole)]2,8-diazanonane diimidamide di HCl.

N'-N''-bis[2-(6-methoxybenzimidazole)]-2,8-diazanonane diimidamide di HCl.

N'-N''-bis[2-benzimidazole]-1,9-diazadecane diimidamide di HCl.

N'-N''-bis[2-(6-chlorobenzimidazole)]-2,9-diazadecane diimidamide di HCl.

N'-N''-bis[2-(6-methylbenzimidazole)]-2,9-diazadecane diimidamide di HCl.

N'-N''-bis[2-(6-nitrobenzimidazole)]-2,9-diazadecane diimidamide di HCl.

N'-N''-bis-[2-(5,6-dimethylbenzimidazole)]-2,9-diazadecane diimidamide di HCl.

N'-N''-[2-(5,6-dichlorobenzimidazole)]-2,9-diazadecane diimidamide di HCl.

N'-N''-bis-[2-(6-carboxybenzimidazole)]-2,9-diazadecane diimidamide di HCl.

N'-N''-bis-[2-(6-methoxybenzimidazole)]-2,9-diazadecane diimidamide di HCl.

N'-N''-bis[2-benzimodazole]-2,9-diazadecane diimidamide di HCl.

N'-N''-bis[2-(6-chlorobenzimidazole)]-2,9-diazadecane diimidamide di HCl.

N'-N''-bis[2-(6-methylbenzimidazole)]-2,9-diazadecane diimidamide di HCl.

N'-N''-bis[2-(6-nitrobenzimidazole)]-2,9-diazadecane diimidamide di HCl.

N'-N''-bis-[2-(5,6-dimethylbenzimidazole)]-2,9-diazadecane diimidamide di HCl.

N'-N''-bis-[2-(5,6-dichlorobenzimidazole)]-2,9-diazadecane diimidamide di HCl.

N'-N''-bis-[2-(6-carboxybenzimidazole)]-2,9-diazadecane diimidamide di HCl.

N'-N''-bis-[2-(6-methoxybenzimidazole)]-2,9-diazadecane diimidamide di HCl.

N'-N''-bis-[2-benzimidazole]-2,10-diazaundecane diimidamide di HCl.

N'-N''-bis-[2-(6-chlorobenzimidazole)]-2,10-diazaundecane diimidamide di HCl.

N'-N''-bis-[2-(6-methylbenzimidazole)]-2,10-diazaundecane diimidamide di HCl. N'-N''-bis[2-(6-nitrobenzimidazole)]-2,10-diazaundecane diimidamide di HCl.

N'-N''-bis-[2-(5,6-dimethylbenzimidazole)]-2,10-diazaundecane diimidamide di HCl.

N'-N''-bis-[2-(5,6-dichlorobenzimidazole)]-2,10-diazaundecane diimidamide di HCl.

N'-N''-bis-[2-(6-carboxybenzimidazole)]-2,10-diazaundecane diimidamide di HCl.

N'-N''-bis-[2-(6-methoxybenzimidazole)]-2,10-diazaundecane diimidamide di HCl.

N'-N''-bis-[2-benzimidazole]-2,11-diazadodecane diimidamide di HCl.

N'-N''-bis-[2-(6-chlorobenzimodazole)]-2,11-diazadodecane diimidamide di HCl.

N'-N''-bis-[2-(6-methylbenzimidazole)]-2,11-diazadodecane diimidamide di HCl.

N'-N''-bis-[2-(6-nitrobenzimidazole)]-2,11-diazadodecane diimidamide di HCl.

N'-N''-bis-[2-(5,6-dimethylbenzimidazole)]-2,11-diazadodecane diimidamide di HCl.

N'-N''-bis-[2-(5,6-dichlorobenzimidazole)]2,11-diazadodecane diimidamide di HCl.

N'-N''-bis-[2-(6-carboxybenzimidazole)]-2,11-diazadodecane diimidamide di HCl.

N'-N'''-bis-[2-(6-methoxybenzimidazole)]-2,11-diazadodecane diimidamide di HCl.

N'-N'''-bis-[2-benzimidazole]-2,12-diazatridecane diimidamide di HCl.

N'-N'''-bis-[2-(6-chlorobenzimidazole)]-2,12-diazatridecane diimidamide di HCl.

N'-N'''-bis-[2-(6-methylbenzimidazole)]-2,12-diazatridecane diimidamide di HCl.

N'-N'''-bis-[2-(6-nitrobenzimidazole)]-2,12-diazatridecane diimidamide di HCl.

N'-N'''-bis-[2-(5,6-dimethylbenzimidazole)]-2,12-diazatridecane diimidamide di HCl.

N'-N'''-bis-[2-(5,6-dichlorobenzimidazole)]-2,12-diazatridecane diimidamide di HCl.

N'-N'''-bis-[2-(6,carboxybenzimidazole)]-2,12-diazatridecane diimidamide di HCl.

N'-N'''-bis-[2-(6-methoxybenzimidazole)]-2,12-diazatridecane diimidamide di HCl.

N'-N'''-bis-[2-benzimidazole]-2,13-diazatetradecane diimidamide di HCl.

N'-N'''-bis-[2-(6-chlorobenzimidazole)]2,13-diazatetradecane diimidamide di HCl.

N'-N'''-bis-[2-(6-methylbenzimidazole)]2,13-diazatetradecane diimidamide di HCl.

N'-N'''-bis-[2-(6-nitrobenzimidazole)]-2,13-diazatetradecane diimidamide di HCl.

N'-N'''-bis-[2-(5,6-dimethylbenzimidazole)]-2,13-diazatetradecane diimidamide di HCl.

N'-N'''-bis-[2-(5,6-dichlorobenzimidazole)]-2,13-diazatetradecane diimidamide di HCl.

N'-N'''-bis-[2-(6,carboxybenzimidazole)]-2,13-diazatetradecane diimidamide di HCl.

N'-N'''-bis-[2-(6-methoxybenzimidazole)]-2,13-diazatridecane diimidamide di HCl.

N'-N'''-bis-[2-imidazolo-(4,5-b) pyridine]-2,5-diazahexane diimidamide di HCl.

N'-N'''-bis-[2-imidazolo-(4,5-b) pyridine]-2,6-diazaheptane diimidamide di HCl.

N'-N'''-bis-[2-imidazolo-(4,5-b) pyridine]-2,7-diazaoctane diimidamide di HCl.

N'-N'''-bis-[2-imidazolo-(4,5-b) pyridine]-2,8-diazanonane diimidamide di HCl.

N'-N'''-bis-[2-imidazolo-(4,5-b) pyridine]-2,9-diazadecane diimidamide di HCl.

N'-N'''-bis-[2-imidazolo-(4,5-b) pyridine]-2,10-diazzundecane diimidamide di HCl.

N'-N'''-bis-[2-imidazolo-(4,5-b) pyridine]-2,11-diazadodecane diimidamide di HCl.

N'-N'''-bis-[2-imidazolo-(4,5-b) pyridine]-2,12-diazatridecane diimidamide di HCl.

N'-N'''-bis-[2-imidazolo-(4,5-b) pyridine]-2,13-diazatetradecane diimidamide di HCl.

N'-N'''-bis-[2-imidazolo-(4,5-c) pyridine]-2,5-diazahexane diimidamide di HCl.

N'-N'''-bis-[2-imidazolo-(4,5-c) pyridine]-2,6-diazaheptane diimidamide di HCl.

N'-N'''-bis-[2-imidazolo-(4,5-c) pyridine]-2,7-diazaoctane diimidamide di HCl.

N'-N'''-bis-[2-imidazolo-(4,5-c) pyridine]-2,8-diazanonane diimidamide di HCl.

N'-N'''-bis-[2-imidazolo-(4,5-c) pyridine]-2,9-diazadecane diimidamide di HCl.

N'-N'''-bis-[2-imidazolo-(4,5-c) pyridine]-2,10-diazaundecane diimidamide di HCl.

N'-N'''-bis-[2-imidazolo-(4,5-c) pyridine]-2,11-diazadodecane diimidamide di HCl.

N'-N'''-bis-[2-imidazolo-(4,5-c) pyridine]-2,12-diazatridecane diimidamide di HCl.

N'-N'''-bis-[2-imidazolo-(4,5-c) pyridine]-2,13-diazatetradecane diimidamide di HCl.

While the invention has been illustrated with respect to particular compounds having antimicrobial activity, it is apparent variations and modifications of the invention can be made.

What is claimed is:

1. A compound of the formula:

$$\begin{array}{c} R \\ \diagdown \\ \text{[imidazo-fused ring]} - C - NH - C - NH - (CH_2)_n - \\ \| \\ NH \end{array}$$

$$\begin{array}{c} R \\ \diagup \\ -NH - C - NH - C - \text{[imidazo-fused ring]} \\ \| \\ NH \end{array}$$

wherein R and $R_1$ = H, lower alkyl, halogen, methoxy, hydroxy, nitro, carboxy, phenyl, phenyl substituted by lower alkyl or sufamyl, where $R_2$ = H, lower alkyl, phenyl or phenyl substituted by lower alkyl, where n is an integer from 2–20, and where x = carbon when y = nitrogen and x = nitrogen when y = carbon.

2. A compound of claim 1 and being selected from the group consisting of

N'-N'''-bis-[2-imidazolo-(4,5-b) pyridine]-2,5-diazahexane diimidamide,

N'-N'''-bis-[2-imidazolo-(4,5-b) pyridine]-2,6-diazaheptane diimidamide,

N'-N'''-bis-[2-imidazolo-(4,5-b) pyridine]-2,7-diazaoctane diimidamide,

N'-N'''-bis-[2-imidazolo-(4,5-b) pyridine]-2,8-diazanonane diimidamide,

N'-N'''-bis-[2-imidazolo-(4,5-b) pyridine]-2,9-diazadecane diimidamide,

N'-N'''-bis-[2-imidazolo-(4,5-b) pyridine]-2,10 diazzundecane diimidamide,

N'-N'''-bis-[2-imidazolo-(4,5-b) pyridine]-2,11-diazadodecane diimidamide,

N'-N'''-bis-[2-imidazolo-(4,5-b) pyridine]-2,12-diazatridecane diimidamide,

N'-N'''-bis-[2-imidazolo-(4,5-b) pyridine]-2,13-diazatetradecane diimidamide,

N'-N'''-bis-[2-imidazolo-(4,5-c) pyridine]-2,5-diazahexane diimidamide,

N'-N'''-bis-[2-imidazolo-(4,5-c) pyridine]-2,6-diazaheptane diimidamide,

N'-N'''-bis-[2,imidazolo-(4,5-c) pyridine]-2,7-diazaoctane diimidamide,

N'-N'''-bis-[2-imidazolo-(4,5-c) pyridine]-2,8-diazanonane diimidamide,

N'-N'''-bis-[2-imidazolo-(4,5-c) pyridine]-2,9-diazadecane diimidamide,

N'-N'''-bis-[2-imidazolo-(4,5-c) pyridine]-2,10-diazaundecane diimidamide,

N'-N'''-bis[2-imidazolo-(4,5-c) pyridine]-2,11-diazadodecane diimidamide,

N'-N'''-bis'-[2-imidazolo-(4,5-c) pyridine]-2,12-diazatridecane diimidamide, and N'-N'''-bis-[2-imidazolo-(4,5-c) pyridine]-2,13-diazatetradecane diimidamide.

* * * * *